(12) United States Patent  
Jones et al.

(10) Patent No.: US 8,999,876 B2
(45) Date of Patent: Apr. 7, 2015

(54) CARBON-SUPPORTED CATALYSTS FOR PRODUCTION OF HIGHER ALCOHOLS FROM SYNGAS

(75) Inventors: Christopher W. Jones, Mableton, GA (US); Pradeep K. Agrawal, Atlanta, GA (US); Tien Thao Nguyen, Viet Hung (VN)

(73) Assignee: Georgia Tech Research Corporation, Atlanta, GA (US)

( * ) Notice: Subject to any disclaimer, the term of this patent is extended or adjusted under 35 U.S.C. 154(b) by 133 days.

(21) Appl. No.: 13/883,681

(22) PCT Filed: Dec. 1, 2011

(86) PCT No.: PCT/US2011/062757
§ 371 (c)(1),
(2), (4) Date: May 6, 2013

(87) PCT Pub. No.: WO2012/078436
PCT Pub. Date: Jun. 14, 2012

(65) Prior Publication Data
US 2013/0245137 A1 Sep. 19, 2013

Related U.S. Application Data

(60) Provisional application No. 61/419,940, filed on Dec. 6, 2010.

(51) Int. Cl.
*B01J 21/18* (2006.01)
*B01J 23/00* (2006.01)
*B01J 27/02* (2006.01)
*B01J 27/051* (2006.01)
*C01B 31/08* (2006.01)
*C07C 27/00* (2006.01)
*C07C 27/06* (2006.01)
*D01F 9/12* (2006.01)
*C07C 29/153* (2006.01)
*B01J 23/28* (2006.01)
*B82Y 30/00* (2011.01)

(52) U.S. Cl.
CPC .............. *C07C 29/153* (2013.01); *B01J 21/185* (2013.01); *B01J 23/007* (2013.01); *B01J 23/28* (2013.01); *B82Y 30/00* (2013.01)

(58) Field of Classification Search
USPC ......... 502/182, 184, 216, 220, 317, 321, 416, 502/418, 427; 518/714, 717; 423/447.1, 423/447.2
See application file for complete search history.

(56) References Cited

U.S. PATENT DOCUMENTS

| | | |
|---|---|---|
| 3,787,332 A | 1/1974 | Sugier |
| 4,126,581 A | 11/1978 | Sugier et al. |
| 4,151,190 A * | 4/1979 | Murchison et al. ............ 518/714 |
| 4,257,920 A | 3/1981 | Sugier et al. |
| 4,346,179 A | 8/1982 | Sugier et al. |
| 4,590,314 A | 5/1986 | Kinkade |
| 4,593,015 A | 6/1986 | Hardman et al. |
| 4,607,055 A | 8/1986 | Grazioso et al. |
| 4,609,678 A | 9/1986 | Hardman et al. |
| 4,661,525 A | 4/1987 | Grazioso et al. |
| 4,675,344 A | 6/1987 | Conway et al. |
| 4,725,625 A | 2/1988 | Simon |
| 4,749,724 A * | 6/1988 | Quarderer et al. ............ 518/714 |
| 4,751,248 A | 6/1988 | Lin et al. |
| 4,752,622 A | 6/1988 | Stevens |
| 4,752,623 A | 6/1988 | Stevens et al. |
| 4,825,013 A | 4/1989 | Quarderer et al. |
| 4,883,533 A | 11/1989 | Kosin et al. |
| 5,627,295 A | 5/1997 | Sofianos et al. |
| 5,851,382 A | 12/1998 | Sudhakar |
| 6,585,948 B1 * | 7/2003 | Ryoo et al. ................. 423/445 R |
| 6,812,187 B1 * | 11/2004 | Pak et al. ...................... 502/180 |
| 6,927,048 B2 | 8/2005 | Verser et al. |
| 7,196,122 B2 | 3/2007 | Ryoo et al. |
| 7,314,960 B1 | 1/2008 | Lin et al. |
| 7,449,425 B2 | 11/2008 | Wang et al. |
| 7,488,699 B2 * | 2/2009 | Huang et al. ................... 502/182 |
| 7,569,318 B2 | 8/2009 | Michel et al. |
| 7,658,776 B1 | 2/2010 | Pearson |
| 7,682,812 B2 | 3/2010 | Verser et al. |
| 7,700,810 B2 | 4/2010 | Kourtakis et al. |
| 7,700,811 B2 | 4/2010 | Kourtakis et al. |
| 7,700,813 B2 | 4/2010 | Kourtakis et al. |
| 7,705,192 B2 | 4/2010 | Kourtakis et al. |
| 7,717,971 B2 | 5/2010 | Aasberg-Petersen et al. |
| 7,718,832 B1 | 5/2010 | Hurley et al. |
| 8,791,043 B2 * | 7/2014 | Pak et al. ...................... 502/182 |

(Continued)

FOREIGN PATENT DOCUMENTS

| | | |
|---|---|---|
| EP | 0119609 A1 | 9/1984 |
| EP | 0149256 A2 | 7/1985 |

(Continued)

OTHER PUBLICATIONS

Abdel-Rahman, International Journal of Energy Research, 1997, vol. 21, Issue 1, p. 31-40.
Bang-Quan, Atmospheric Environment, 2003, vol. 37, p. 4965-4971.
Bao, Topics in Catalysis, 2009, vol. 52, p. 789-794.
Bezemer, Chemical Communications, 2005, p. 731-733.
Cavani, Catalysis Today, 1991, vol. 11, Issue 2, p. 173-301.
Christensen, Applied Catalysis A: General, 2009, vol. 366, Issue 1, p. 29-43.
Cortes-Jacome, Catalysis Today, 2008, vol. 130, p. 56-62.

(Continued)

*Primary Examiner* — Patricia L Hailey

(57) ABSTRACT

Catalyst compositions comprising molybdenum, sulfur and an alkali metal ion supported on a nanofibrous, mesoporous carbon molecular sieve are useful for converting syngas to higher alcohols. The compositions are produced via impregnation and may enhance selectivity to ethanol in particular.

8 Claims, No Drawings

(56) References Cited

U.S. PATENT DOCUMENTS

| | | |
|---|---|---|
| 2007/0004588 A1 | 1/2007 | Wang et al. |
| 2010/0022806 A1* | 1/2010 | Meitzner .................. 568/840 |
| 2010/0075837 A1 | 3/2010 | Meitzner et al. |
| 2010/0280287 A1 | 11/2010 | Kharas et al. |

FOREIGN PATENT DOCUMENTS

| | | | | |
|---|---|---|---|---|
| EP | 0172431 | | 2/1986 | |
| WO | WO-2007/127479 A2 | | 11/2007 | |
| WO | 2012/078436 | * | 6/2012 | ............... B01J 23/00 |
| WO | 2012/078437 | * | 6/2012 | ............... B01J 23/00 |

OTHER PUBLICATIONS

Danilov, Chemistry and Technology of Fuels and Oils, 2001, vol. 37, Issue 6, p. 444-455.
Fan, Catalysis Today, 2009, vol. 147, p. 86-93.
Fang, Catalysis Today, 2009, vol. 147, Issue 2, 133-138.
Forzatti, Catalysis Reviews: Science and Engineering, 1991, vol. 33, Issue 1&2, p. 109-168.
Gomez-Hortigu, Journal of the American Chemical Society, 2009, vol. 131, p. 16509-16524.
Haider, Journal of Catalysis, 2009, vol. 261, Issue 1, p. 9-16.
Herman, Catalysis Today, 2000, vol. 55, Issue 3, p. 233-245.
Iranmahboob, Applied Catalysis A: General, 2002, vol. 231, p. 99-108.
Iranmahboob, Applied Catalysis A: General, 2003, vol. 247, Issue 2, p. 207-218.
Jiao, Journal of Catalysis, 2008, vol. 260, 342-350.
Jun, Journal of the American Chemical Society, 2000, vol. 122, p. 10712-10719.
Juncheng, The Journal of Physical Chemistry C, 2007, vol. 111, p. 12038-12044.
Li, Fuel Processing Technology, 2007, 88, 125-127.
Li, Topics in Catalysis, 2005, vol. 32, Issue 3-4, p. 233-239.
Mallada, Applied Catalysis A: General, 2002, vol. 231, p. 109-116.
McDonald, Microporous and Mesoporous Materials, 2009, vol. 120, p. 263-266.
Morrill, Catal. Lett, 2012, vol. 142, p. 875-881.
Nunan, Journal of Catalysis, 1989, vol. 116, p. 195-221.
Nunan, Journal of Catalysis, 1989, vol. 116, p. 222-229.
Olson, Energy and Environmental Research Center: Semi-Annal Report Jan. 1-Jun. 30, 1996.
Perez-Ramirez, Chemistry: A European Journal, 2007, vol. 13, 870-878.
Sathish, Chemistry of Materials, 2007, vol. 19 p. 2398-2400.
Sels, Catalysis Reviews: Science and Engineering, 2001, vol. 43, Issue 4, p. 444-488.
Shen, The Journal of Physical Chemistry C, 2008, vol. 112, p. 13114-13120.
Songhai, The Journal of Physical Chemistry B, 2004, vol. 108, p. 11561-11566.
Sreenath, Bioresource Technology, 2000, vol. 72, 253-260.
Surisetty, Applied Catalysis A: General, 2009, vol. 365, Issue 2, p. 243-251.
Surisetty, Applied Catalysis A: General, 2010, vol. 381, Issue 1-2, p. 282-288.
Tien-Thao, Applied Catalysis A: General, 2006, vol. 311, p. 204-212.
Tien-Thao, Journal of Catalysis, 2007, vol. 245, Issue 2, p. 348-357.
Toebes, Catalysis Today, 2002, vol. 76, p. 33-42.
Van Laar, Journal of Catalysis, 2001, vol. 197, p. 139-150.
Woo, Journal of Catalysis, 1993, vol. 192, p. 672-690.
Wu, Applied Catalysis A: General, 2008, vol. 340, Issue 1, p. 87-97.
Wu, Chemistry of Materials, 2007, vol. 19, p. 1577-1583.
Zavoianu, Applied Catalysis A: General, 2005, vol. 286, p. 211-220.
Zhang, Chemical Communications, 2010, vol. 46, 862-864.
PCT/US2011/062757, International Preliminary Report on Patentability.
PCT/US2011/062757, International Search Report and Written Opinion of the International Searching Authority.
PCT/US2011/062757, Response to Search Report and Written Opinion.
PCT/US2011/062757, Response to Second Written Opinion.
PCT/US2011/062757, Written Opinion of the International Preliminary Examining Authority.
PCT/US2011/062760 International Search Report and Written Opinion of the International Searching Authority.
PCT/US2011/062760, International Preliminary Report on Patentability.
PCT/US2011/062760 second Written Opinion of the International Searching Authority.
PCT/US2011/062760 Response to Second Written Opinion.
PCT/US2011/062760, Response to Search Report and Written Opinion.

* cited by examiner

CARBON-SUPPORTED CATALYSTS FOR PRODUCTION OF HIGHER ALCOHOLS FROM SYNGAS

This application is a non-provisional application claiming priority from the U.S. Provisional Patent Application No. 61/419,940, filed on Dec. 6, 2010, entitled "CARBON-SUPPORTED CATALYSTS FOR PRODUCTION OF HIGHER ALCOHOLS FROM SYNGAS," the teachings of which are incorporated by reference herein as if reproduced in full hereinbelow.

Additionally, this application is a National Phase of International Patent Application No. PCT/US2001/062757, filed on Dec. 1, 2011, and published as WO 2012/078436.

BACKGROUND

1. Field of the Invention

The present invention relates to catalytic processes for conversion of syngas to alcohols. More particularly, it relates to molybdenum-based catalysts, supported on nanodimensional carbon materials, showing improved selectivity toward higher alcohols.

2. Background of the Art

A variety of alcohols, particularly those ranging from methanol to hexanol (C1-6OH), are products that can be synthesized from synthesis gas. This gas, also called "syngas," is a mixture of hydrogen gas and carbon monoxide gas ($H_2$/CO)). The C1-C6 alcohols in particular are considered to be important synthetic fuels and chemicals. In general, alcohols which are defined herein as "higher alcohols," i.e., alcohols having at least two carbon atoms ($C2^+$), are currently sought to serve as, in particular, automobile fuels and fuel blends. In this application many offer desirably high octane numbers as well as desirably low emissions of nitrogen oxide ($NO_x$), ozone, CO, and aromatic vapors. In addition, the higher alcohols ($C2^+OH$) may be useful as alternative feedstocks for commercially significant olefins (produced via dehydration of the higher alcohol), particularly when the syngas is derived from biomass or coal.

Unfortunately, not all conversion processes provide desirable selectivity to specific higher alcohols. Researchers have identified various means and methods to alter the selectivity. One obvious way is to use different catalysts. Known catalyst compositions to produce alcohols have included combinations of copper, zinc oxide, and alumina ($Cu/ZnO/Al_2O_3$); molybdenum sulfide ($MoS_2$); cobalt and copper (Co—Cu); rhenium (Rh); and molybdenum carbide ($Mo_2C$). Each of these will produce various combinations of selectivities. Among these useful catalysts is, for example, the catalyst disclosed in U.S. Pat. No. 5,627,295, which is based on copper-aluminum-zinc (Cu—Al—Zn) and another element selected from Group IIIA, IIIB, IVA, or IVB. U.S. Pat. No. 7,449,425 discloses using catalysts which comprise a noble metal and certain transition metals on magnesium-aluminum (Mg—Al) hydrotalcite supports.

Molybdenum-based catalysts (e.g., $MoS_2$, $Mo_2C$), including $MoS_2$ promoted by alkali metal ions, have also been shown to improve ethanol selectivity. For example, U.S. Pat. Nos. 4,661,525 and 4,825,013 disclose methods for making a mixture of C2-C6 aliphatic alcohols by reacting carbon monoxide with hydrogen over alkali-doped $MoS_2$ catalysts modified by the addition of an element of Group VIIIB (e.g., Co, Fe, or Ni). Alkali metal promoters, such as sodium (Na), potassium (K), cesium (Cs), or rubidium (Rb), mixed with cobalt-molybdenum-sulfur (Co—Mo—S) compositions have also been investigated for syngas conversion. U.S Patent Application 2010/007583718 describes a way to intercalate a strong basic promoter such as K, Cs, barium (Ba), strontium (Sr), scandium (Sc), lanthanum (La), or cerium (Ce) into layered $MoS_2$ to prepare a basic catalyst for conversion of syngas. U.S. Pat. No. 4,675,344 discloses manipulation of hydrogen sulfide ($H_2S$) concentration in the syngas feed to improve selectivity to higher alcohols versus methanol. U.S. Pat. No. 4,749,724 discloses use of alkali-doped $MoS_2$ supported on activated carbon having a Brunauer-Emmett-Teller (BET) surface area ranging from 100 to 1,500 square meters per gram ($m^2/g$).

Recently, researchers working in the field of materials chemistry have been successful in synthesizing new nanostructured materials, such as Mg—Si fishbone-like oxides, MgO nanosheets, nanoporous aluminophosphates, nanotubular titania and silica, nickel phyllosilicate nanotubes, and carbon nanosheets, nanofibers, and nanowhiskers. Some initial attempts to employ carbon nanotubes, mesoporous carbon structures, and carbon nanofibers as suitable supports for the conversion of syngas to liquid fuels have been recently disclosed. In the art it is common for the terms "nanoporous" and "mesoporous" to be used interchangeably to refer to the presence of nanodimensional pores.

Despite such attempts, there remains a need in the art for a method of converting syngas to higher alcohols that offers further improved selectivity to, in particular, ethanol.

SUMMARY OF THE INVENTION

In one embodiment the invention provides a catalyst composition comprising molybdenum, sulfur and an alkali metal ion on a nanofibrous, mesoporous carbon molecular sieve support.

In another embodiment the invention provides a process for making a catalyst composition comprising impregnating a nanofibrous, mesoporous carbon molecular sieve support with molybdenum, sulfur and an alkali metal ion.

In still another embodiment the invention provides a process for converting a mixture of hydrogen gas and carbon monoxide gas to at least one higher alcohol comprising contacting, under conditions suitable to form at least one higher alcohol, a gas mixture, including at least hydrogen gas and carbon monoxide gas, and a catalyst composition including molybdenum, sulfur and an alkali metal ion supported on a nanofibrous, mesoporous carbon molecular sieve support.

DETAILED DESCRIPTION OF THE EMBODIMENTS

The present invention includes a catalyst composition that is particularly useful for the synthesis of ethanol and other higher alcohols, i.e., $C2^+$ alcohols, from syngas, herein defined as any mixture consisting of or including both $H_2$ and CO gases. This catalyst composition comprises an alkali metal, molybdenum and sulfur, all which are on a nanofibrous, mesoporous carbon molecular sieve support. The nanofibrous carbon molecular sieve support may, in particular embodiments, possess properties including, for example, high chemical resistance and high thermal stability in an inert atmosphere. However, the compositions may also exhibit additional advantageous features, such as a pore volume ranging from 0.8 to 1.7 cubic centimeters per gram ($cm^3/g$); a BET surface area ranging from 300 to 1,500 square meters per gram ($m^2/g$); and an average pore diameter ranging from 3.0 to 5.0 nanometers (nm).

The mesoporous carbon molecular sieve support is, in particular embodiments, carbon nanofibers constructed of ordered nanowires, i.e., structures of essentially solid columnar configuration, of substantially uniform size. Transmission electron micrography (TEM) images show the molecular sieves as groups of nanofibers structured to contain mesopores, i.e., the nanofibers form cylinders of hexagonal cross-section, having mesoporous internal diameter spaces. As the terms are used herein, "nanofiber(s)" and "nanofibrous" refer to structures having a fibrous morphology and an average cross-sectional diameter ranging from 1 to 100 nm, while the terms "mesopore(s)" and "mesoporous" refer to an opening or cavity in the nanofibrous structure that has an average internal diameter that is capable of admitting a molecule. In certain embodiments the average internal diameter of the opening or cavity ranges from 2 to 20 nm, but may range from slightly less than 1 nm to slightly less than 100 nm, depending upon the average cross-sectional diameter of the nanofiber. Thus, both fibers and pores are nanodimensional.

These carbon molecular sieve supports may be prepared using any effective mesoporous template, which may be, for example, a silica, an aluminosilicate, an aluminophosphate, an oxide, or a combination thereof. In particular embodiments, useful templates include mesoporous oxides, preferably exhibiting uniformity in both arrangement and pore size, into and onto which a carbon source may be infiltrated and then pyrolyzed to form a carbon structure. The template is then removed, and the resulting free-standing carbon structure is essentially a negative replica of the mesoporous oxide template. Preparation may be carried out desirably in a two-step process, wherein the first step is making the template and the second step is using the template to make the carbon molecular sieve support. Alternatively, the template may be purchased or obtained from another source, and then employed to form the carbon molecular sieve support.

For example, one suitable template is silica having a well-ordered hexagonal arrangement of mesopores of approximately 7 to 10 nm average diameter. This template may be synthesized by the hydrolysis of tetraethylorthosilicate (TEOS) in an aqueous solution containing an amount of hydrochloric acid (hydrogen chloride, HCl) and a structure-directing agent such as PLURONIC™ P-123, which is a triblock copolymer [poly(ethylene glycol)-block-poly(propylene glycol)-block-poly(ethylene glycol), having the formula $HO(CH_2CH_2O)_{20}(CH_2CH(CH)O)_{70}(CH_2CH_2O)_{20}H)]$ that is available from BASF Corporation. The resulting mixture may be stirred at a desired temperature, for example, from 25 degrees Celsius (° C.) to 40° C., preferably 35° C., before aging at a higher temperature, for example, from 60° C. to 180° C., over a period ranging from 1 to 2 days. During the aging time, a precipitate containing surfactant-filled pores forms and may then be filtered to remove the water and subsequently dried in air at room temperature. The recovered solid may then be calcined in an oven at a temperature ranging from 500° C. to 700° C., which removes the surfactant from the pores and results in an open-pore silica molecular sieve which is suitable as a template.

Confirmation that the calcined template has the desired mesoporous character and therefore can serve as an effective template for the carbon molecular sieve support used in the invention may be obtained via powder X-ray diffraction (XRD) and nitrogen ($N_2$) physisorption. XRD shows three characteristic reflection peaks, at angle 2-theta, at approximately 0.8, 1.4, and 1.7, which are indexed as (100), (110), and (200) planes. The template powder's BET surface area preferably ranges from 300 to 1,500 $m^2/g$, and in certain embodiments from 600 to 1,000 $m^2/g$. This product may be used directly as a silica template for the carbon molecular sieve support.

The second step in preparing the carbon molecular sieve support used in the inventive catalyst compositions involves impregnating a carbon source, such as a carbohydrate solution, with the template. This template may be the prepared silica template, as described hereinabove, or may be any other suitable template. In this step an aqueous solution may be first prepared including the carbon source and an inorganic acid, which serves as a catalyst for the polymerization of carbon monomers under synthesis conditions. For example, a monosaccharide, such as glucose, fructose, sucrose, or a combination thereof, may be useful as the carbon source, and the inorganic acid may be selected from, for example, hydrochloric (HCl), sulfuric ($H_2SO_4$), phosphoric ($H_3PO_4$), nitric ($HNO_3$), or a combination thereof. In this reaction the aqueous solution may then be added to the template, which in this embodiment is in dry form, thereby forming a slurry. In desirable embodiments this may be most conveniently carried out at a temperature ranging from 20° C. to 50° C., preferably from 20° C. to 30° C. Ambient temperature is therefore usually most convenient. The carbon source is added to the mesopores of the silica template until the pores are nearly completely filled. In the presence of the inorganic acid the carbon atoms therein begin to polymerize, eventually forming the organic polymer that constitutes the structure of the carbon molecular sieve support. See, for example, *J. Am. Chem. Soc.*, 122 (2000), which is incorporated herein by reference in its entirety.

The slurry may then be thermally treated to ensure that polymerization is maximized A temperature ranging from 80° C. to 120° C. is preferable to accomplish this, for a period of time ranging from 4 to 8 hours, and in many embodiments a temperature of 100° C. for approximately 6 hours is effective. Following this thermal treatment the polymerizing sample may be held, for a period of time that is similar in length (i.e., from 4 to 8, preferably 8, hours), at a higher temperature, for example, from 140° C. to 180° C. During this time the slurry may turn dark brown or black, indicating complete polymerization of any carbon source, e.g., a monosaccharide, which is present in the pores of the silica template.

Following the completion of the polymerization the slurry may then be pyrolyzed to ensure that most of the non-carbon materials are removed from the template. In many embodiments this may be accomplished most effectively under vacuum or in an inert atmosphere. For this pyrolysis, a desirable temperature may range from 700° C. to 1,100° C.

In a final substep of preparation of the carbon molecular sieve support, the resulting pyrolyzed solid may be treated with a solution capable of dissolving the silica template. For example, an aqueous solution of hydrofluoric acid (HF) or a strong base such as sodium hydroxide (NaOH) or potassium hydroxide (KOH) may be effectively used. The solution etches, i.e., dissolves, the template from the carbon molecular sieve support, and the material may then be dried to attain its final form as a stable molecular sieve support. Because the particular silica template used in the embodiment described hereinabove contains an array of aligned, similarly-sized mesopores in which the carbon from the carbon source polymerizes, arrays of carbon nanowires, forming carbon nanofibers, are left behind when the template is removed.

Confirmation that the final product is, indeed, the desired carbon molecular sieve support may be obtained by means including, for example, X-ray diffraction (XRD), TEM, $N_2$ physisorption, and BET analysis thereof. Characterization using small-angle copper alpha radiation powder XRD shows a sharp peak, i.e., a d-spacing, for angle 2-theta at approximately 1.0, typically indexed as the (100) plane of the twodimensional hexagonal structure. The adsorption/desorption isotherm in $N_2$ physisorption analysis is typically of Type IV. The BET surface area is desirably in the range of from 300 to 1,500 $m^2/g$, more desirably from 1,100 to 1,500 $m^2/g$; the pore volume may range from 0.8 to 1.7 $cm^3/g$, more desirably from 0.85 to 1.2 $cm^3/g$; and the average pore diameter may range from 3.0 to 5.0 nm, more desirably from 3.4 to 4.2 nm. TEM shows the ordered structure of the carbon molecular sieve support as a negative replica of the starting silica template.

Once the nanofibrous, mesoporous carbon molecular sieve support has been prepared or obtained, it is ready to use to prepare the inventive catalyst compositions. In these compositions the carbon molecular sieve support is impregnated using a molybdenum (Mo) source and an alkali metal ion source. The alkali metal ion source may be any providing an ion selected from sodium ($Na^+$), potassium ($K^+$), cesium ($Cs^{2+}$), and combinations thereof. Sulfur (S) is also included in the catalyst composition, and may be, but is not necessarily, combined therein with Mo as $MoS_2$. Thus, the S source may be included with the Mo source initially, or, in another embodiment, the catalyst composition, in its unsulfided (without $MoS_2$, but with Mo) form, may be treated with hydrogen sulfide ($H_2S$) as the S source after loading of the Mo and alkali metal ion, and before or during (or both) employing the catalyst composition in reactions such as, but not limited to, the conversion of syngas to higher alcohols. It is desirable that the mole ratio of molybdenum to alkali metal ion fall within the range of from 3:1 to 1:3.

In order to accomplish the impregnation, the selected Mo source, preferably a soluble Mo salt, such as ammonium heptamolybdate (($NH_4$)$_6$$Mo_7$$O_{24}$$\cdot$$4H_2O$)), is first incorporated in an aqueous solution, which then contacts the carbon molecular sieve support at a desired temperature. For most purposes the concentration of Mo in the solution is in the range of from 0.40 to 1.5 molar (M), depending upon the desired level of Mo loading in the catalyst compositions. Contact between the Mo source and the carbon molecular sieve support desirably occurs at a temperature ranging from 40° C. to 120° C., and more desirably from 60° C. to 80° C. The impregnated carbon molecular sieve support may then be dried and heated, preferably at a temperature ranging from 100° C. to 500° C., to remove the water and decompose the Mo source, which will create molybdenum dioxide ($MoO_2$) and/or molybdenum trioxide ($MoO_3$) domains on the surfaces of the molecular sieve.

Before or after impregnation with the molybdenum, an alkali metal is also loaded, in ionic form, onto the carbon molecular sieve support. As is the case of the Mo source, the alkali metal ion source is also desirably a soluble salt, enabling it to be dissolved in an aqueous solution such that the alkali metal cation is at a molar concentration ranging, in particular embodiments, from 0.40 to 1.5 M. For this purpose it is desirable that the carbon molecular sieve support contact the solution at a temperature ranging from 100° C. to 500° C., and more desirably from 250° C. to 400° C. The carbon molecular sieve support, now impregnated with both Mo and K, may then be dried and heated, preferably at a temperature ranging from 300° C. to 500° C. and in an inert atmosphere, such as an $N_2$ flow, in order to remove the water.

The resulting catalyst compositions, which include the alkali metal ion promoter, may now be described by the general formula "[alkali metal]/Mo/carbon support," e.g., "K/Mo/carbon support" and, in particular embodiments, may also be in its sulfided, i.e., $MoS_2$-containing, form. It is desirably composed of from 0.1 to 20 wt % of Mo and from 0.3 to 15 wt % alkali metal. As before, its structure and character may be confirmed by means such as powder XRD, $N_2$ physisorption, and TEM analyses. Such may be characterized by powder XRD analysis, indicating the presence of strong reflections (peaks) at angle 2-theta of 26.1; 36.9; and 53.8, which are characteristic of $MoO_2$, as well as weak reflections at angle 2-theta of 23.3; 27.3; 34.4; 39.1; 46.2; 49.2; 49.3; 52.7; 55.1; and 58.8, corresponding to potassium molybdates including $K_2Mo_2O_7$; $K_2Mo_4O_6$; and $K_2Mo_7O_{20}$ where potassium is the selected alkali metal. The BET surface area of the promoted catalyst K/Mo/carbon support desirably ranges from 300 to 1,500 $m^2/g$, and in particular embodiments from 1,100 to 1,500 $m^2/g$. TEM analysis shows well-dispersed molybdenum oxide particles on carbon nanofibers. The average diameter of the molybdenum oxide (usually dioxide) particles ranges from 20 to 60 nm. At the lower Mo loadings, XRD peaks may not be visible.

The inventive catalyst compositions may be used to form higher alcohols ($C2^+OH$) from syngas. Syngas having low $H_2/CO$ ratios may be particularly useful, and may be obtained from a hydrocarbon feed stock such as oil, coal, natural gas or biomass. The mole ratio of $H_2$ to CO is desirably from 0.1 to 5 moles of $H_2$ per mole of CO, with a preferred mole ratio being from 0.5 to 2.

If the catalyst composition has not been sulfided prior to placement in a suitable catalyst bed for syngas conversion, it may be sulfided either after placement and before use as a catalyst, or during use. This can be done preferably in the reactor where the higher alcohols will be formed, where the catalyst may be situated in a fixed bed, moving bed, or fluidized bed arrangement. In some embodiments, pre-sulfidation may be carried out by flowing a 20 vol % $H_2S$/80 vol % $H_2$ gas over the catalyst. This pre-sulfidation may be effectively carried out at a temperature ranging from 200° C. to 700° C., desirably 400° C. to 500° C., for a time period ranging from 1 to 3 hours. In some embodiments, that temperature may be attained by ramping from ambient temperature at a rate of, for example, 5° C. per minute (° C./min). Once the pre-sulfidation is completed, the reactor may be treated with a flow of inert gas until the temperature reaches a desired reaction temperature for the conversion of the syngas to higher alcohols. Under these conditions, a small concentration of $H_2S$ is also typically included with the syngas flow, for example, from 5 to 200 parts per million (ppm), which helps to maintain the sulfidation level.

In an alternative approach, sulfidation may be carried out concurrently with the higher alcohols production, by including a larger portion of $H_2S$ with the syngas flow. In this case, the amount of $H_2S$ included with the syngas flow may range from 0.001 vol % to 0.1 vol % and eventually results in formation of an $MoS_2$ component in situ. To ensure that the sulfidation is optimized, either as a pre-sulfidation or in situ during the higher alcohols production process, a sample of the sulfided composition may be analyzed by powder XRD. The appearance of broad reflections at angle 2-theta of 14.4; 32.2; 39.3; and 58.3; shows the presence of $MoS_2$, when the Mo loading is greater than or equal to 10 wt %. At a lower molybdenum loading, no XRD reflections are typically observed, but Extended X-Ray Absorption Fine Structure (EXAFS) and X-Ray Photoelectron Spectroscopy (XPS) analysis may be used to confirm structure and morphology and suggests the presence of finely-dispersed $MoS_2$ in the pores and on the carbon molecular sieve support. The BET surface area of the sulfided catalyst may range, in particular embodiments, from 300 to 1,500 $m^2/g$, and in particular embodiments from 1,100 to 1,500 $m^2/g$, i.e., approximately the same surface area range as the non-sulfided catalyst.

In certain embodiments the syngas may be converted into higher alcohols over the inventive catalyst compositions at a reaction temperature ranging from 235° C. to 360° C. Pressures may range, in particular embodiments, from about 1,000 pounds per square inch (psi) to 2,500 psi (6.89 to 17.24 megapascals (MPa). The gas hourly space velocity (GHSV) may range from 4,000 to 12,000 milliliters per gram per hour (mL/g/h), while the mole ratio of $H_2$ to CO may range from about 1:4 to 4:1. $N_2$ may be used as an internal standard from which the CO conversion can be calculated. The conversion is also calculated from the overall carbon mass balance of the reaction. The conversion of CO determined in this way may range from 5 to 40 mole percent (mol %). Selectivity to ethanol and higher alcohols, based on carbon atoms, may range from 40 to 80 mol %, with the selectivity to ethanol ranging from 30 to 50 mol %, excluding carbon dioxide ($CO_2$). In general, methanol selectivity may tend to be lower than ethanol selectivity. In many embodiments methane may be the major hydrocarbon formed, and selectivity thereto may range from 10 to 30 mol %, excluding $CO_2$.

EXAMPLES

Example 1

Preparation of the Mesoporous Carbon Molecular Sieve Support

A silica molecular sieve template is synthesized from tetraethylorthosilicate (TEOS) using triblock copolymer PLURONIC™ P-12343. A quantity of 8.79 grams (g) of the PLURONIC™ P-12343 is added into a 500 milliliter (mL) flask containing 300 mL of deionized (DI) water and 48.24 g of 10 normal (N) HCl. The solution is stirred at 35° C. for 2 hours (h) before adding 17.32 g of TEOS slowly. The synthetic solution is sealed and aged at 35° C. with stirring for 24 h, and then aged at 75° C. in an oven for 48 h. After cooling to room temperature, the precipitate is filtered and washed with DI water. The filter cake is dried in air at room temperature overnight before calcining at 550° C. for 6 h in air at a ramp of 2° C. per minute (° C./min) to remove the organic agents.

A mass of 5 g of mesoporous silica template is impregnated with a solution containing 10 g of DI water, 0.72 g of $H_2SO_4$, and 6.25 g of sucrose ($C_{12}H_{22}O_{11}$). The mixture is then dried at 100° C. for 6 h in air before heating to 160° C. for 6 h at a ramp of 10° C./min Then, the solid is carbonized in a flow of 50 milliliters per minute (mL/min) of nitrogen ($N_2$) at 900° C. for 2 h at a ramp of 2° C./min, then is subsequently washed with 5 wt % HF solution at least twice before drying in an oven at 105° C. overnight. The dried mesoporous carbon molecular sieve support has a BET surface area of 1,390 $m^2$/g.

Example 2

Preparation of Catalyst Composition A

First, a solution containing 1.31 g of ammonium heptamolybdate (($NH_4$)$_6Mo_7O_{24}$.4$H_2O$) and 5.0 g of DI water is stirred at 65° C. for 2 h. Then, 2.50 g of the mesoporous carbon molecular sieve support described in Example 1 is added to the preheated solution. The resultant mixture is kept at 75° C. for 2 h before drying in an oven at 105° C. overnight. The resulting black powder is heated in a 0.5-inch (in) diameter quartz tube at 500° C. for 2 h at a ramp of 5° C./min in a flow of 50 mL/min of $N_2$.

The heated solid is then added into 5.0 g of DI water containing 0.514 g of potassium carbonate ($K_2CO_3$) at room temperature. The wet solid is dried in an oven at 10° C. overnight, and then calcined in a 0.5-in diameter quartz tube at 400° C. for an hour at a ramp of 5° C./min in a flow of 50 mL/min of $N_2$. The molybdenum loading calculated as $MoO_3$ is about 30 wt % and the $K_2CO_3$ loading is about 15 wt %. The BET surface area of the calcined catalyst is 317 $m^2$/g. XRD shows presence of strong reflections indicating $MoO_2$ at (2-theta): 26.2; and 37.4; reflections indicating $K_2Mo_7O_{20}$ (2-theta, low intensity ("weak")): 23.2; 36.7; 51.9; 64.1; and 65.0.

Example 3

Preparation of Catalyst Composition B

First, a solution containing 0.595 g of ammonium heptamolybdate (($NH_4$)$_6Mo_7O_{24}$.4$H_2O$) and 4.0 g of DI water is stirred at 65° C. for 2 h. A quantity of 1.95 g of the mesoporous carbon molecular sieve support described in Example 1 is then added to the preheated solution. The resultant mixture is kept at 75° C. for 2 h before drying in an oven at 105° C. overnight. The resulting black powder is heated in a 0.5-in diameter quartz tube at 500° C. for 2 h at a ramp of 5° C./min in a flow of 50 mL/min of $N_2$. The heated solid is then added into 4.0 g of DI water containing 0.23 g of $K_2CO_3$ at room temperature. The wet solid is dried in an oven at 10° C. overnight, and then calcined in a 0.5-in diameter quartz tube at 400° C. for an hour at a ramp of 5° C./min in a flow of 50 mL/min of $N_2$. The molybdenum loading calculated as $MoO_3$ is about 20 wt % and the $K_2CO_3$ loading is about 10 wt %. BET surface area of the calcined catalyst is 771 $m^2$/g. XRD: $MoO_2$ (2-theta): 26.0; 37.4; and 53.0; $K_2Mo_2O_7$ (2-theta, low intensity): 27.2; 28.4; and 36.9.

Example 4

Preparation of Catalyst Composition C

First, a solution containing 0.108 g of ammonium heptamolybdate (($NH_4$)$_6Mo_7O_{24}$.4$H_2O$) and 1.5 g of DI water is stirred at 65° C. for 2 h. A quantity of 0.78 g of the mesoporous carbon molecular sieve support described in Example 1 is added into the preheated solution. The mixture is kept at 75° C. for 2 h before drying in an oven at 105° C. overnight. The resulting powder is heated in a 0.5-in diameter quartz tube at 500° C. for 2 h at a ramp of 5° C./min in a flow of 50 mL/min of $N_2$.

The heated solid is then added to 1.5 g of DI water containing 0.043 g of $K_2CO_3$ at room temperature. The wet solid is dried in an oven at 105° C. overnight, and then calcined in a 0.5-in diameter quartz tube at 400° C. for an hour at a ramp of 5° C./min in a flow of 50 mL/min of $N_2$. The molybdenum loading calculated as $MoO_3$ is about 10 wt % and the $K_2CO_3$ loading is about 5 wt %. BET surface area of the calcined catalyst is 535 $m^2$/g. XRD: $K_2Mo_2O_7$ (2-theta, low intensity): 27.6, 42.5, and 43.7.

Example 5

Preparation of Catalyst Composition D

First, a solution containing 0.55 g of ammonium heptamolybdate (($NH_4$)$_6Mo_7O_{24}$.4$H_2O$) and 3.5 g of DI water is stirred at 65° C. for 2 h. An amount of 1.80 g of the mesoporous carbon molecular sieve support described in Example 1 is added into the preheated solution. The mixture is kept at 75° C. for 2 h before drying in an oven at 105° C. overnight. The resulting black powder is heated in a 0.5-in diameter quartz tube at 500° C. for 2 hours at a ramp of 5° C./min in a flow of 50 mL/min of $N_2$.

The heated solid is then added into 3.5 g of DI water containing 0.645 g of $K_2CO_3$ at room temperature. The wet solid is dried in an oven at 105° C. overnight, and then calcined in a 0.5-in diameter quartz tube at 400° C. for 1 h at a ramp of 5° C./min in a flow of 50 mL/min of $N_2$. The molybdenum loading calculated as $MoO_3$ is about 20 wt % and the $K_2CO_3$ loading is about 30 wt %. BET surface area of the calcined catalyst is 446 $m^2$/g. XRD: $MoO_2$ (2-theta): 25.7; 37.9; 53.9; and 60.4; $K_2Mo_2O_7$, $K_2Mo_4O_6$, $K_2Mo_7O_{20}$ (2-theta): 23.3; 27.3; 34.4; 39.1; 46.2; 49.2; 49.3; 52.7; 55.1; 58.8; 62.8; and 64.5.

Example 6

Production of Higher Alcohols

The reactor consists of a 0.25-in stainless steel (316 SS) tube with a catalyst composition loading of 0.20 g. Premixed $H_2$, CO, and $N_2$ feed gases from cylinders are compressed and regulated at the reaction pressure stated in Tables 1, 2 and 3. The feed gas mixture contains $H_2$ and CO at a molar ratio of 1/1, with about 10 percent by volume (vol %) of $N_2$ to serve as an internal standard, and about 50 ppm of $H_2S$. The mixed feed gas passes through a bed of zeolite 13X molecular sieve at 170° C. to remove iron (Fe) and any other carbonyl contaminants that may be present in the CO portion of the feed. The feed gas then flows at the GHSVs stated in each of the Tables, through the fixed bed reactor kept at each stated reaction temperature and under a pressure of 1,500 pounds per square inch gauge (psig) (10.34 MPa) to form product effluent.

The reactor effluent is fed into a gas chromatograph to analyze the product distribution, with the resulting catalytic activity ("Productivity") expressed as the weight, in milligrams, of an individual product divided by the weight, in grams, of the catalyst (cat) per hour (mg/g cat/h), as shown in Tables 1-3, with Table 3 illustrating the effect of varying GHSVs for a single catalyst composition, Catalyst Composition D. "Product selectivity" (based on carbon mole percent (mol % C), excluding $CO_2$), is defined as the total of carbon atoms in each product divided by the sum of carbon atoms in all the alcohols (including methanol and higher alcohols), non-alcohol oxygenates, and hydrocarbons. Hydrocarbons ("HC") are mainly methane ($CH_4$), and oxygenates ("Oxy") are the total of oxygen-containing products excluding all alcohols. The catalyst compositions of the invention show a productivity of higher alcohols ($C2^+OH$) ranging from 38.2 to 115 mg/g cat/h at a temperature ranging from 285° C. to 310° C. and a GHSV of 6,000 mL/g/h.

TABLE 1

| | | | Product Selectivity (C, %) | | | | | Productivity (mg/g cat/h) | |
|---|---|---|---|---|---|---|---|---|---|
| Cat. | CO Conv. (%) | $CO_2$ (%) | MeOH | EtOH | C3 + OH | Oxy | HC | MeOH | $C2^+OH$ |
| A | 7.1 | 23.8 | 21.8 | 41.2 | 11.9 | 5.7 | 19.4 | 32.3 | 54.7 |
| B | 5.0 | 28.9 | 20.1 | 46.1 | 10.9 | 3.0 | 16.2 | 19.9 | 41.6 |
| C | 4.3 | 26.5 | 15.5 | 50.4 | 14.2 | 4.4 | 15.4 | 14.7 | 42.4 |

GHSV = 6,000 mL/g/h; Temperature (° C.) = 285; $H_2$/CO = 1; $H_2S$ (ppm) = 50; catalyst weight = 0.20 g.

TABLE 2

| | | | Product selectivity (C, %) | | | | | Productivity (mg/g cat/h) | |
|---|---|---|---|---|---|---|---|---|---|
| Cat. | CO Conv. (%) | $CO_2$ (%) | MeOH | EtOH | C3 + OH | Oxy | HC | MeOH | $C2^+OH$ |
| A | 16.3 | 24.8 | 17.8 | 36.3 | 11.5 | 2.8 | 31.7 | 76.8 | 115.7 |
| B | 14.0 | 27.2 | 10.1 | 29.1 | 7.4 | 3.2 | 46.2 | 26.5 | 73.6 |
| C | 10.8 | 29.7 | 9.6 | 39.3 | 15.5 | 1.9 | 33.3 | 19.9 | 78.6 |

GHSV = 6,000 mL/g/h; Temperature (° C.) = 310; $H_2$/CO = 1; $H_2S$ (ppm) = 50; catalyst weight = 0.20 g.

TABLE 3

Catalyst Composition D

| | | | Product selectivity (C, %) | | | | | Productivity (mg/g cat/h) | |
|---|---|---|---|---|---|---|---|---|---|
| GHSV | CO Conv (%) | $CO_2$ (%) | MeOH | EtOH | C3 + OH | Oxy | HC | MeOH | $C2^+OH$ |
| 4,500 | 6.6 | 32.9 | 4.9 | 33.3 | 22.2 | 4.1 | 35.3 | 4.5 | 33.7 |
| 6,000 | 4.8 | 33.1 | 9.7 | 43.5 | 21.3 | 5.1 | 20.4 | 8.4 | 38.2 |
| 9,000 | 3.1 | 34.4 | 11.9 | 45.3 | 21.9 | 5.5 | 15.3 | 9.8 | 37.9 |
| 12,000 | 2.6 | 31.2 | 13.7 | 43.3 | 19.7 | 5.6 | 17.7 | 13.3 | 41.8 |

Temperature (° C.) = 310; $H_2$/CO = 1; $H_2S$ (ppm) = 50; catalyst weight = 0.20 g.

What is claimed is:

1. A catalyst composition comprising molybdenum, sulfur and an alkali metal ion on a nanofibrous, mesoporous carbon molecular sieve support.

2. The catalyst composition of claim 1 wherein the alkali metal ion is selected from the group of ions consisting of sodium, potassium, cesium, and combinations thereof, the molybdenum and the sulfur are combined as molybdenum sulfide, or both.

3. The catalyst composition of claim 1 wherein X-ray powder diffraction analysis exhibits strong reflections at angle 2-theta of 26.1; 36.9; and 53.8, and weak reflections at angle 2-theta of 23.3; 27.3; 34.4; 39.1; 46.2; 49.2; 49.3; 52.7; 55.1; and 58.8.

4. The catalyst composition of claim 1 wherein Brunauer-Emmett-Teller analysis shows a surface area from 300 to 1,000 $m^2/g$.

5. A process for making the catalyst composition of claim 1 comprising impregnating a nanofibrous, mesoporous carbon molecular sieve support with molybdenum, sulfur and an alkali metal ion.

6. The process of claim 5 wherein the nanofibrous, mesoporous carbon molecular sieve support is prepared by (a) contacting a mesoporous silica template with a carbon source under conditions suitable to absorb the carbon source into the mesorporous silica template and polymerize the carbon source to form a nanofibrous, mesoporous carbon structure; (b) removing the mesoporous silica template by contacting the nanofibrous, mesoporous carbon structure with an aqueous acid or base under conditions suitable to dissolve the mesoporous silica template and obtain a nanofibrous, mesoporous carbon molecular sieve support; and (c) recovering the nanofibrous, mesoporous carbon molecular sieve support.

7. A process for converting a mixture of hydrogen gas and carbon monoxide gas to at least one higher alcohol comprising contacting, under conditions suitable to form at least one higher alcohol, a gas mixture, including at least hydrogen gas and carbon monoxide gas, and the catalyst composition of claim 1.

8. The process of claim 7 wherein, at a gas hourly space velocity of 6,000 mL/g/h, the catalyst composition exhibits a productivity of the at least one higher alcohol ranging from 38.2 to 115.7 mg/g catalyst/h.

* * * * *